US00PP27496P2

(12) United States Plant Patent
van den Hoogen

(10) Patent No.: US PP27,496 P2
(45) Date of Patent: Dec. 20, 2016

(54) ***MONARDA* PLANT NAMED 'ALLBELL'**

(50) Latin Name: *Monarda didyma*
Varietal Denomination: Allbell

(71) Applicant: Wilhelmus T. J. van den Hoogen, Cuijk (NL)

(72) Inventor: Wilhelmus T. J. van den Hoogen, Cuijk (NL)

(73) Assignee: Allplants Holding B.V., Cuijk (NL)

( * ) Notice: Subject to any disclaimer, the term of this patent is extended or adjusted under 35 U.S.C. 154(b) by 105 days.

(21) Appl. No.: 14/544,620

(22) Filed: Jan. 28, 2015

(51) Int. Cl.
*A01H 5/02* (2006.01)

(52) U.S. Cl.
USPC ..... Plt./455

(58) Field of Classification Search
USPC ..... Plt./455
See application file for complete search history.

*Primary Examiner* — Susan McCormick Ewoldt
(74) *Attorney, Agent, or Firm* — C. A. Whealy

(57) ABSTRACT

A new and distinct cultivar of *Monarda* plant named 'Allbell', characterized by its upright plant habit; dark green-colored leaves; freely flowering habit; red purple-colored flowers; and good postproduction longevity.

1 Drawing Sheet

Botanical designation: *Monarda didyma.*
Cultivar denomination: 'ALLBELL'.

BACKGROUND OF THE INVENTION

The present invention relates to a new and distinct cultivar of *Monarda* plant, botanically known as *Monarda didyma*, typically grown as a cut flower and hereinafter referred to by the name 'Allbell'.

The new *Monarda* plant is a product of a planned breeding program conducted by the Inventor in Cuijk, The Netherlands. The objective of the breeding program is to create new *Monarda* plants with attractive flowers and good postproduction longevity.

The new *Monarda* plant originated from an open-pollination in September, 2011 of a proprietary selection of *Monarda didyma* identified as code number 11-6-2, not patented, as the female, or seed, parent with an unknown selection of *Monarda didyma*, as the male, or pollen, parent. The new *Monarda* plant was discovered and selected by the Inventor as a single flowering plant from within the progeny of the stated open-pollination grown in a controlled nursery environment in Cuijk, The Netherlands in September, 2012.

Asexual reproduction of the new *Monarda* plant by softwood cuttings in Cuijk, The Netherlands, since April, 2013 has shown that the unique features of this new *Monarda* plant are stable and reproduced true to type in successive generations.

SUMMARY OF THE INVENTION

Plants of the new *Monarda* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Allbell'.

These characteristics in combination distinguish 'Allbell' as a new and distinct *Monarda* plant:

1. Upright plant habit.
2. Dark green-colored leaves.
3. Freely flowering habit.
4. Red purple-colored flowers.
5. Good postproduction longevity.

Plants of the new *Monarda* differ primarily from plants of the female parent selection in the following characteristics:

1. Plants of the new *Monarda* have darker green-colored leaves than plants of the female parent selection.
2. Plants of the new *Monarda* and the female parent selection differ in flower color as plants of the female parent selection have purple pink-colored flowers.

Plants of the new *Monarda* can be compared to plants of *Monarda didyma* 'Saxon Purple', not patented. In side-by-side comparisons plants of the new *Monarda* differ from plants of 'Saxon Purple' in the following characteristics:

1. Plants of the new *Monarda* have darker green-colored leaves than plants of 'Saxon Purple'.
2. Plants of the new *Monarda* and 'Saxon Purple' differ in flower color as plants of 'Saxon Purple' have bluish purple-colored flowers.

BRIEF DESCRIPTION OF THE PHOTOGRAPH

The accompanying colored photograph illustrates the overall appearance of the new *Monarda* plant showing the colors as true as it is reasonably possible to obtain in colored reproductions of this type. Colors in the photograph may differ slightly from the color values cited in the detailed botanical description which accurately describe the actual colors of the new *Monarda* plant.

The photograph is a side perspective view of a typical flowering plant of 'Allbell'.

DETAILED BOTANICAL DESCRIPTION

The aforementioned photograph and following observations, measurements and values describe plants grown during August in ground beds in an outdoor nursery in Nakuru, Kenya and under cultural practices typical of commercial cut flower *Monarda* production. During the production of the plants, day temperatures ranged from 15° C. to 25° C. and night temperatures ranged from 5° C. to 15° C. Plants were six months old when the photograph and the description were taken. In the detailed description, color references are made to The Royal Horticultural Society Colour Chart, 2007 Edition, except where general terms of ordinary dictionary significance are used.

Botanical classification: *Monarda didyma* 'Allbell'.

Parentage:

*Female, or seed, parent*.—Proprietary selection of *Monarda didyma* identified as code number 11-6-2, not patented.

*Male, or pollen, parent*.—Unknown selection of *Monarda didyma*, not patented.

Propagation:

*Type cutting*.—By softwood cuttings.

*Time to initiate roots, summer*.—About 10 to 14 days at temperatures ranging from 12° C. to 30° C.

*Time to produce a rooted young plant, summer*.—About four to six weeks at temperatures ranging from 12° C. to 30° C.

*Root description*.—Fine, fibrous; white in color.

*Rooting habit*.—Freely branching; medium density.

Plant description:

*Plant and growth habit*.—Herbaceous perennial; upright plant form; moderately vigorous growth habit.

*Plant height*.—About 105 cm.

*Plant width*.—About 34.5 cm.

*Branch description*.—Branching habit: Freely basal branching habit with few lateral branches. Length: About 91.9 cm. Diameter: About 4 mm. Internode length: About 11.7 cm. Strength: Strong. Aspect: Mostly upright. Texture: Sparsely to moderately pubescent. Luster: Slightly glossy. Color: Close to 144C.

Leaf description:

*Arrangement*.—Opposite, simple.

*Length*.—About 10.4 cm.

*Width*.—About 5.4 cm.

*Shape*.—Ovate.

*Apex*.—Apiculate.

*Base*.—Obtuse to short attenuate.

*Margin*.—Serrate.

*Texture, upper and lower surfaces*.—Moderately pubescent; slightly rough.

*Luster, upper and lower surfaces*.—Glossy.

*Venation pattern*.—Pinnate.

*Fragrance*.—Moderately fragrant; pleasant, spicy.

*Color*.—Developing leaves, upper surface: Close to 137B. Developing leaves, lower surface: Close to 138A. Fully expanded leaves, upper surface: Close to N137A; venation, close to 177D. Fully expanded leaves, lower surface: Close to 138A; venation, close to 145B.

*Petioles*.—Length: About 2.7 cm. Diameter: About 2 mm. Color, upper surface: Close to 177D. Color, lower surface: Close to 145B.

Flower description:

*Flower form, arrangement and flowering habit*.—Single labiate flowers arranged in terminal globular spikes; flowers face outwardly; freely flowering habit with about 96 flowers developing per inflorescence; flowers sessile.

*Natural flowering season*.—Long flowering habit, plants flower from mid-July to mid-September in The Netherlands.

*Postproduction longevity*.—Cut flowering stems maintain good substance for about one to two weeks; flowers not persistent.

*Fragrance*.—Moderately fragrant; pleasant, spicy.

*Flower buds*.—Length: About 1.3 cm. Diameter: About 1.5 mm. Shape: Narrowly oblanceolate; curved. Color: Close to 64A to 64B; immature calyx, close to N186C and towards the base, close to 59D.

*Inflorescence height*.—About 5.1 cm.

*Inflorescence diameter*.—About 6.5 cm.

*Flower length* (*vertical*).—About 1.7 cm.

*Flower diameter* (*horizontal*.—About 6 mm.

*Flower depth* (*height*).—About 3.4 cm.

*Petals*.—Arrangement: Labiate; upper lip hooded; lower lip, a single lobe; lips fused 55% of total length. Length, upper and lower lips: About 3.2 cm. Width, upper lip: About 1.5 mm. Width, lower lip: About 7 mm. Shape, upper lip: Lanceolate; apex, emarginate. Shape, lower lip: Oblanceolate; apex, caudate. Margin, upper and lower lips: Entire; lower petal, undulate. Texture, upper and lower lips, upper and lower surfaces: Moderately pubescent. Luster, upper and lower lips, upper and lower surfaces: Dull, matted. Color, upper lip: When opening, upper and lower surfaces: Close to 60C. Fully opened, upper and lower surfaces: Close to 60C; color does not fade with development. Color, lower lip: When opening, upper surface: Close to N57A. When opening, lower surface: Close to 60D. Fully opened, upper surface: Close to N57B; color does not fade with development. Fully opened, lower surface: Close to 60D; color does not fade with development.

*Sepals*.—Arrangement: About five in a single whorl; lower 85% fused into a tubular calyx. Length: About 1.05 cm. Width: About 1 mm. Apex: Narrowly acute. Margin: Entire. Texture, upper and lower surfaces: Pubescent. Color: When opening, upper and lower surfaces: Close to N186C; towards the base, close to 59D. Fully opened, upper and lower surfaces: Close to N186C; towards the base, close to 185C.

*Inflorescence bracts*.—Quantity and arrangement: About 18 at the base of inflorescence. Length: About 3.9 cm. Width: About 1.7 cm. Shape: Ovate to narrowly ovate; apex, acute. Margin: Entire. Texture, upper and lower surfaces: Pubescent. Color: When opening and fully opened, upper surface: Close to 147A; venation, close to 64A. When opening and fully opened, lower surface: Close to 137B; venation, close to 152D.

*Reproductive organs*.—Stamens: Quantity per flower: Two. Filament length: About 1.5 cm. Filament color: Close to 73C. Anther length: About 1.5 mm. Anther shape: Narrowly elliptic. Anther color: Close to N77B. Pollen amount: Moderate. Pollen color: Close to 156D. Pistils: Quantity per flower: One. Pistil length: About 3.4 cm. Stigma shape: Cleft, unequal. Stigma color: Close to 72B. Style length: About 3.1 cm. Style color: Close to N74C; towards the base, close to 155A. Ovary color: Close to 145D.

*Seed and fruit*.—Seed and fruit production have not been observed on plants of the new *Monarda*.

Disease & pest resistance: Plants of the new *Monarda* not been observed to be resistant to pathogens and pests common to *Monarda* plants.

Garden performance: Plants of the new *Monarda* have exhibited good tolerance to rain, wind and high temperatures about 30° C. and to be hardy to USDA Hardiness Zone 5.

It is claimed:

1. A new and distinct *Monarda* plant named 'Allbell' as illustrated and described.

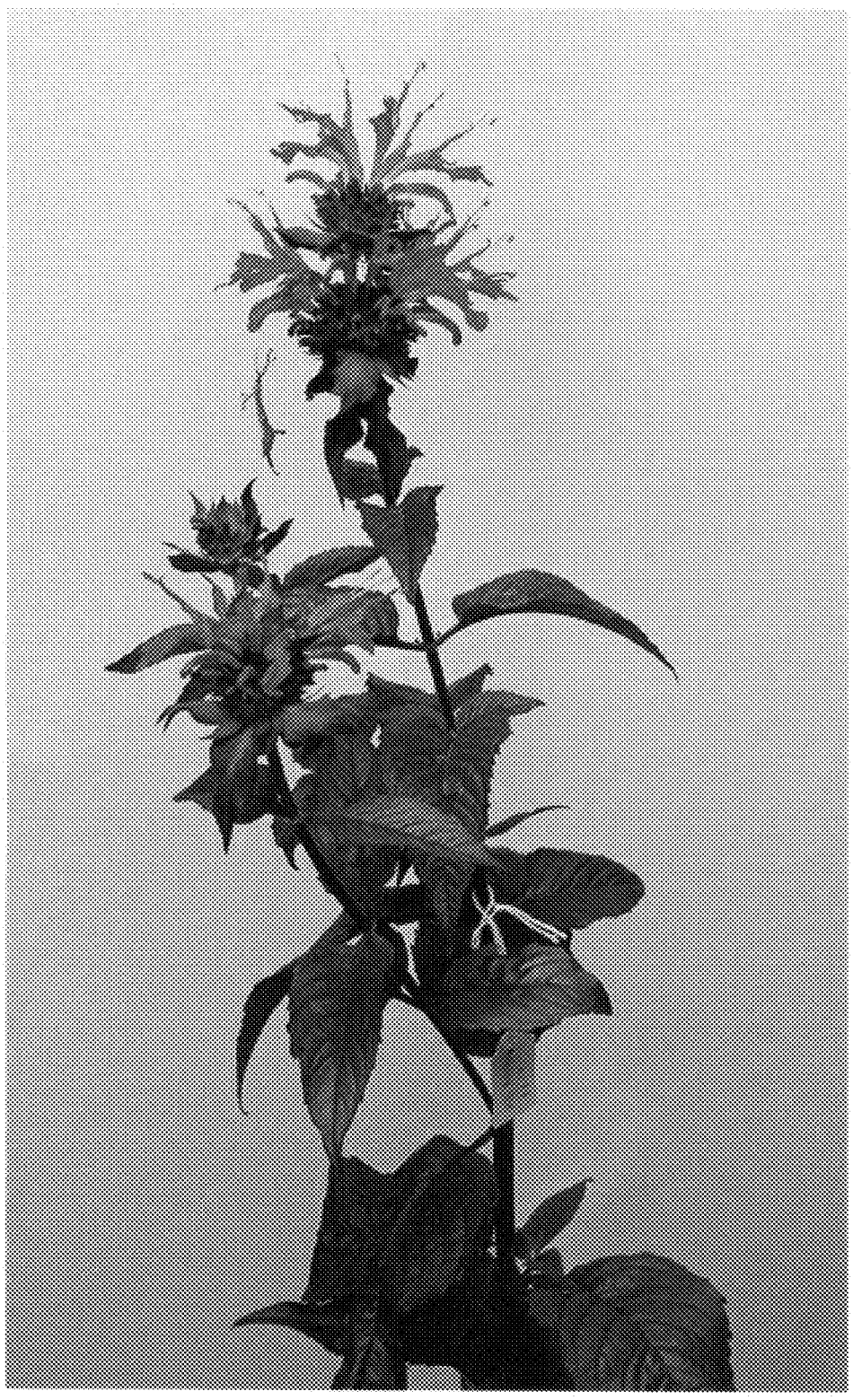

* * * * *